(12) United States Patent
Tomic-Edgar et al.

(10) Patent No.: US 6,277,144 B1
(45) Date of Patent: *Aug. 21, 2001

(54) THERMAL CONDITIONING APPARATUS

(75) Inventors: Kerry Tomic-Edgar, Santa Ana; Gordon Shigezawa, Irvine; Anthony V. Beran, Santa Ana, all of CA (US)

(73) Assignee: Respiratory Support Products, Inc., Irvine, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/167,663

(22) Filed: Oct. 7, 1998

(51) Int. Cl.$^7$ ....................................................... A61F 7/00
(52) U.S. Cl. ........................................... 607/108; 607/112
(58) Field of Search .............................. 607/96, 108, 109, 607/110, 111, 112; 165/46; 5/421, 423

(56) References Cited

U.S. PATENT DOCUMENTS

| | | |
|---|---|---|
| D. 359,810 | 6/1995 | Namenye ............................ D24/206 |
| D. 362,507 | 9/1995 | Zuck et al. ......................... D24/206 |
| 1,004,192 | 9/1911 | Phelan . |
| 1,777,982 | 10/1930 | Popp . |
| 1,965,424 | 7/1934 | Mascolo . |
| 2,512,559 | 6/1950 | Williams ................................. 5/347 |
| 2,579,964 | 12/1951 | Reynolds .............................. 219/19 |
| 2,601,189 | 6/1952 | Wales, Jr. ................................ 4/160 |
| 2,706,988 | 4/1955 | Weber . |
| 2,930,594 | 3/1960 | MacCracken ........................ 257/306 |
| 2,991,627 | 7/1961 | Suits ......................................... 62/3 |
| 2,998,817 | 9/1961 | Armstrong . |
| 3,418,726 | 12/1968 | Sparks ....................................... 34/99 |
| 3,444,922 | 5/1969 | Dingman ............................... 165/26 |
| 3,610,323 | 10/1971 | Troyer .................................... 165/46 |
| 3,691,646 | 9/1972 | Ruffolo .................................... 34/90 |
| 3,714,947 | 2/1973 | Hardy . |
| 3,757,366 | 9/1973 | Sacher ..................................... 5/347 |
| 3,778,851 | 12/1973 | Howorth ................................. 5/347 |
| 3,854,156 | 12/1974 | Williams ................................. 5/347 |
| 3,867,939 | 2/1975 | Moore et al. ......................... 128/254 |
| 3,881,477 | 5/1975 | Von Otto . |
| 3,908,655 | 9/1975 | Lund . |
| 3,942,202 | 3/1976 | Chevrolet ................................ 5/348 |
| 4,121,571 | 10/1978 | Pickering . |

(List continued on next page.)

FOREIGN PATENT DOCUMENTS

| | | |
|---|---|---|
| 113420 | 7/1984 | (EP) . |
| 0 311 336 A1 | 4/1989 | (EP) . |
| WO 97/14381 | 4/1997 | (WO) . |

Primary Examiner—Linda C. M. Dvorak
Assistant Examiner—R. Kearney
(74) Attorney, Agent, or Firm—Price and Gess

(57) ABSTRACT

The present invention relates to an improved thermal conditioning apparatus for thermally treating a patient. More specifically, the present invention relates to an inflatable apparatus for bathing a patient with a thermally conditioned medium. Such a treatment apparatus is useful for medically treating a patient suffering from hypothermia or hyperthermia, or for maintaining the body temperature of a patient undergoing a surgical procedure. A thermal conditioning apparatus according to the present invention includes first and second pluralities of orifices, the first plurality of orifices being smaller than the second plurality. An inlet portion which receives the thermal conditioning medium is located closer to the first plurality of orifices than the second plurality of orifices. The combined use of smaller orifices in close proximity to the inlet portion with larger orifices distal from the inlet portion tends to minimize the thermal gradients that may occur. Furthermore, a thermal conditioning apparatus according to the present invention includes a cover portion formed from the first and second material layers which make up the thermal conditioning apparatus.

27 Claims, 5 Drawing Sheets

U.S. PATENT DOCUMENTS

| | | | |
|---|---|---|---|
| 4,136,413 | 1/1979 | Scales | 5/365 |
| 4,139,004 | 2/1979 | Gonzalez, Jr. . | |
| 4,149,541 | 4/1979 | Gammons et al. . | |
| 4,398,535 | 8/1983 | Guibert . | |
| 4,540,412 | 9/1985 | Van Overloop | 604/291 |
| 4,660,388 | 4/1987 | Greene, Jr. | 62/261 |
| 4,753,241 | 6/1988 | Brannigan et al. . | |
| 4,807,644 | 2/1989 | Sandhaus | 128/849 |
| 4,844,072 | 7/1989 | French et al. . | |
| 4,867,230 | 9/1989 | Voss | 165/46 |
| 4,871,900 | 10/1989 | Hickman | 219/366 |
| 4,907,308 | 3/1990 | Leininger et al. | 5/455 |
| 4,971,056 | 11/1990 | Seacord . | |
| 5,044,364 | 9/1991 | Crowther . | |
| 5,097,829 | 3/1992 | Quisenberry . | |
| 5,125,238 | 6/1992 | Ragan et al. | 62/259.3 |
| 5,165,400 | 11/1992 | Berke . | |
| 5,168,589 | 12/1992 | Stroh et al. | 5/455 |
| 5,184,612 | 2/1993 | Augustine . | |
| 5,265,599 | 11/1993 | Stephenson et al. | 607/104 |
| 5,300,098 | 4/1994 | Philipot | 607/96 |
| 5,300,101 | 4/1994 | Augustine et al. | 607/107 |
| 5,300,102 | 4/1994 | Augustine et al. | 607/107 |
| 5,304,213 | 4/1994 | Berke et al. | 607/104 |
| 5,304,217 | 4/1994 | Stephenson et al. | 607/114 |
| 5,324,320 | 6/1994 | Augustine et al. | 607/107 |
| 5,336,250 | 8/1994 | Augustine | 607/107 |
| 5,343,579 | 9/1994 | Dickerhoff et al. | 5/421 |
| 5,350,417 | 9/1994 | Augustine | 607/104 |
| 5,360,439 | 11/1994 | Dickerhoff et al. | 607/104 |
| 5,383,918 | 1/1995 | Panetta | 607/104 |
| 5,392,847 | 2/1995 | Stephenson | 165/46 |
| 5,405,370 | 4/1995 | Irani | 607/104 |
| 5,443,488 | 8/1995 | Namenye et al. | 607/104 |
| 5,545,194 | 8/1996 | Augustine | 607/104 |
| 5,620,482 | 4/1997 | Augustine et al. | 607/107 |
| 5,632,769 | 5/1997 | Kappel et al. | 607/104 |
| 5,643,337 | 7/1997 | Kappel et al. | 607/107 |
| 5,658,325 | 8/1997 | Augustine | 607/107 |
| 5,674,269 | 10/1997 | Augustine | 607/107 |
| 5,675,848 | 10/1997 | Kappel | 5/482 |
| 5,697,963 | 12/1997 | Augustine | 607/108 |
| 5,733,318 | 3/1998 | Augustine | 607/104 |
| 5,891,187 * | 4/1999 | Winthrop et al. | 607/96 |

* cited by examiner

THERMAL CONDITIONING APPARATUS

BACKGROUND OF THE INVENTION

1. Field of Invention

The present invention relates to an improved thermal conditioning apparatus for thermally treating a patient. More specifically, the present invention relates to an inflatable apparatus for bathing a patient with a thermally conditioned medium. Such a treatment apparatus is useful for medically treating a patient suffering from hypothermia or hyperthermia, or for maintaining the body temperature of a patient undergoing a surgical procedure.

2. Description of Related Art

Conventional patient thermal treatment systems suffer from several disadvantages. First, conventional patient thermal treatment systems fail to deliver the thermal medium to the patient without encumbering access to the patient's body. Next, conventional patient thermal treatment systems are difficult to manufacture, consisting of numerous parts requiring a time-consuming, labor-intensive, and costly manufacturing process to assemble into a completed system. Finally, conventional patient thermal treatment systems are thermally inefficient in treating patients. With conventional patient thermal treatment systems, patients are subjected to large thermal gradients within the thermal treatment apparatus, causing undesirable hot-spots or cool zones.

Accordingly, there is a need for an improved thermal conditioning apparatus for treating a patient which is inexpensive, easy to manufacture, flexible in its operation, and provides a more uniform thermal treatment.

SUMMARY OF THE INVENTION

Accordingly, the present invention is directed to an improved thermal conditioning apparatus for treating a patient which substantially eliminates one or more of the problems or disadvantages found in the prior art.

An object of the present invention is to provide for an improved thermal conditioning apparatus for treating a patient which is inexpensive.

Another object of the present invention is to provide for an improved thermal conditioning apparatus for treating a patient which is easy to manufacture.

Another object of the present invention is to provide for an improved thermal conditioning apparatus for treating a patient which allows for compact storage prior to its use.

Another object of the present invention is to provide for an improved thermal conditioning apparatus for treating a patient which is flexible in its operation.

Another object of the present invention is to provide for an improved thermal conditioning apparatus for treating a patient which delivers a more uniform thermal treatment.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the invention, as embodied and broadly described, the invention contemplates a thermal conditioning apparatus for delivering a thermal medium to a patient including a first material layer having a substantially planar configuration and including a first and second plurality of orifices, the first plurality of orifices being smaller than the second plurality; a second material layer having a substantially planar configuration, the first material layer bonded to the second material layer at portions thereof to define an inflatable medium delivery space therebetween; and an inlet portion in connection with the medium delivery space to receive a thermally conditioned medium and disposed closer to the first plurality of orifices than to the second plurality of orifices wherein a lower volume of thermal medium is delivered to the patient through the first plurality and a higher volume of thermal medium is delivered to the patient through the second plurality.

In another aspect, the invention contemplates a thermal conditioning apparatus for delivering a thermal medium to a patient including a first material layer having a substantially planar configuration; a second material layer having a substantially planar configuration, the first material layer bonded to the second material layer at portions thereof to define an inflatable medium delivery space therebetween; an inlet portion in connection with the medium delivery space to receive a thermally conditioned medium; a plurality of orifices to deliver the thermally conditioned medium to the patient; and a cover portion formed from the first and second material layers wherein the cover portion is adapted to cover at least a portion of the patient in the conditioning apparatus.

It is to be understood that both the general description above, and the following detailed description are exemplary and explanatory and are intended to provide further explanation of the invention as claimed.

BRIEF DESCRIPTION OF THE DRAWINGS

The accompanying drawings which are included to provide a further understanding of the invention and constitute a part of this specification, illustrate embodiments of the invention and together with the written description, serve to explain the principles of the invention. In the drawings.

DETAILED DESCRIPTION OF THE PREFERRED EMBODIMENTS

Figure 1A:
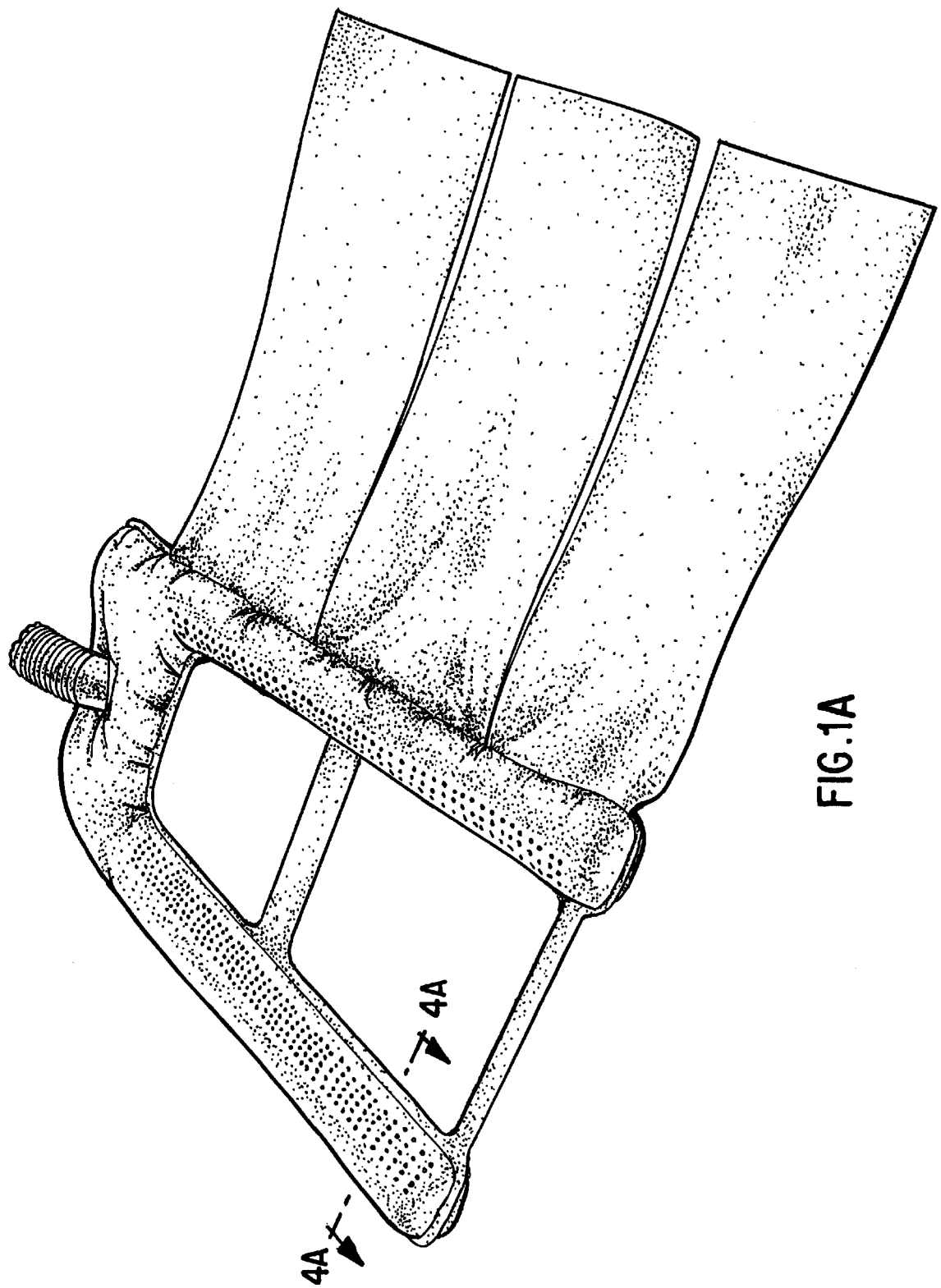
FIG. 1A is an isometric view of a preferred embodiment of a thermal conditioning apparatus for delivering a thermal medium to a patient according to the present invention in an inflated state.

Reference will now be made in detail to the preferred embodiments of the present invention, examples of which are illustrated in the accompanying drawings. For example, FIG. 1A shows an isometric view of a thermal conditioning apparatus for delivering a thermal medium to a patient according to the present invention in an inflated state.

The thermal conditioning apparatus generally includes a first material layer and a second material layer, each having a substantially planar configuration. A first material layer 110 and a second material layer 120 may be constructed of any appropriate material. For example, the first material layer 110 and the second material layer 120 may be constructed of any non-permeable, soft material suited for inflation and contact with a patient's body. Preferably, each of the first material layer 110 and the second material layer 120 are constructed both of a soft external surface layer for contact with a patient's body and a coating layer to provide the necessary non-permeability for inflation.

The material layers of the thermal conditioning apparatus are bonded at desired portions to define an inflatable medium delivery space. In particular, FIG. 1A shows that the first material layer 110 and the second material layer 120 are bonded together at the bonding areas 140 to form an inflatable medium delivery space 102. Furthermore, thermal conditioning apparatus includes an inlet portion in connection with the medium delivery space to receive a thermally conditioned medium. As shown in FIG. 1A, the thermal conditioning apparatus 100 includes an inlet portion 150 which cooperates with a thermal medium delivery hose 165 and a thermal medium supply unit 160 (not shown) to inflate the medium delivery space 102. The thermal conditioning apparatus 100 also includes a plurality of orifices 130 to deliver the thermally conditioned medium to the patient. Still further, the thermal conditioning apparatus 100 includes a cover portion 170 adapted to cover at least a portion of the patient in the conditioning apparatus 100. The cover portion 170 may be constructed of any appropriate material. For example, the cover portion 170 may be constructed of any thermally insulative material. Preferably, the cover portion 170 is constructed of the first material layer 110 and the second material layer 120.

The thermal conditioning apparatus preferably further includes first and second material layers which are further bonded to form a header portion and a pair of extending portions disposed at ends of the header portion, within the medium delivery space. For example, FIG. 1A shows that the first material layer 110 and the second material layer 120 bonded together at the bonding areas 140 to form a header portion 104, a left extending portion 106, and a right extending portion 108. The thermal conditioning apparatus includes two extending portions which each extend linearly from a different end of the header portion. An example of this is illustrated in FIG. 1A, wherein the left extending portion 106 and the right extending portion 108 each extend from a different end of the header portion 104. Furthermore, the thermal conditioning apparatus for delivering a thermal medium to a patient according to the objects of the present invention includes a plurality of orifices located on the pair of extending portions and an inlet portion located on the header portion. For example, as shown in FIG. 1A, the plurality of orifices 130 extend longitudinally along the left extending portion 106 and the right extending portion 108. Furthermore, the inlet portion 150 is preferably centrally located on the header portion 104. Note that the plurality of orifices 130 are separated from the inlet portion 150 by several inches to ensure that the patient is not directly exposed to the fluid entering the inlet portion 150. Preferably the plurality of orifices 130 are separated from the inlet portion 150 by at least three inches in distance.

Although a single inlet portion 150 is shown, the thermal conditioning apparatus 100 could have several inlet portions located along the header portion 104. Each inlet portion would remain sealed until a thermal medium delivery hose 165 was inserted into that particular inlet. This would provide further flexibility to the thermal conditioning apparatus 100.

The thermal conditioning apparatus may include at least one under-patient strip portion disposed between the pair of extending portions. For example, as illustrated in FIG. 1A, under-patient strip portions 180 and 190 are disposed between the left extending portion 106 and the right extending portion 108. The under-patient strip portions 180 and 190 provide added structural stability for the thermal conditioning apparatus 100. The under-patient strip portions 180 and 190 also prevent fluids which come off of the patient from pooling and coming into contact with the patient. Instead such fluids run directly onto the surface below the patient and are then carried away.

As depicted in FIG. 1A, the under-patient strip portions 180 and 190 are bounded by the bonding portions 140 and are thus non-inflatable. The under-patient strip portions 180 and 190 may be constructed of any appropriate material. For example, the under-patient strip portions 180 and 190 may be constructed of any soft material suited for contact with a patient's body. Preferably, the under-patient strip portions 180 and 190 are each constructed of the first material layer 110 and the second material layer 120.

Figure 1B:
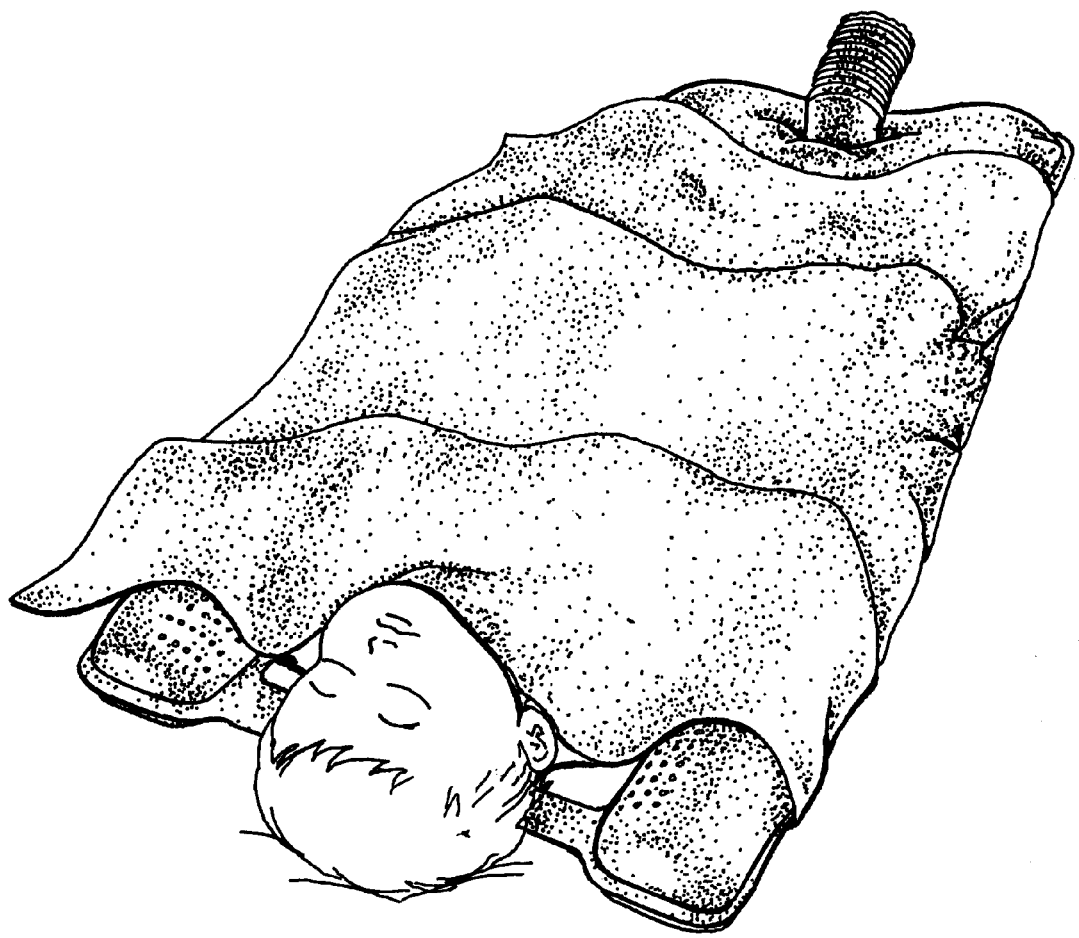
FIG. 1B is an isometric view of a preferred embodiment of a thermal conditioning apparatus for delivering a thermal medium to a patient according to the present invention in an inflated state showing a patient and the cover portions in a closed position.

FIG. 1B is an isometric view of a thermal conditioning apparatus for delivering a thermal medium to a patient according to the present invention in an inflated state showing a patient and the cover portions in a closed position. Thus, the operation of a thermal conditioning apparatus for delivering a thermal medium to a patient according to the present invention is readily apparent from FIG. 1B. In operation, a patient 1 in need of thermal conditioning (suffering from hypothermia or hyperthermia, or undergoing a surgical procedure) is placed lengthwise in the thermal conditioning apparatus 100. The patient's head or feet, dependent upon whichever position best optimizes use and satisfies the particular access requirements, can be placed in proximity to the header portion 104. Note that the patient 1 is placed on top of the under-patient strip portions 180 and 190. If access to the patient's body is not needed, the cover portion 170 is placed over the patient. Selective access to different regions of the patient's body is provided by the plurality of flaps that comprise the cover portion 170. The thermal medium supplied by the thermal medium supply unit 160 (not shown) passes through the thermal medium delivery hose 165 through an appropriate connector (i.e., a right angle connector) and into the inlet portion 150. Thus, the thermal medium which enters the inlet portion 150 causes the medium delivery space 102, including the header portion 104, the left extending portion 106, and the right extending portion 108 to inflate. Thus, thermal medium is delivered to the patient via the plurality of orifices 130 formed in the left extending portion 106 and the right extending portion 108.

Figure 2:
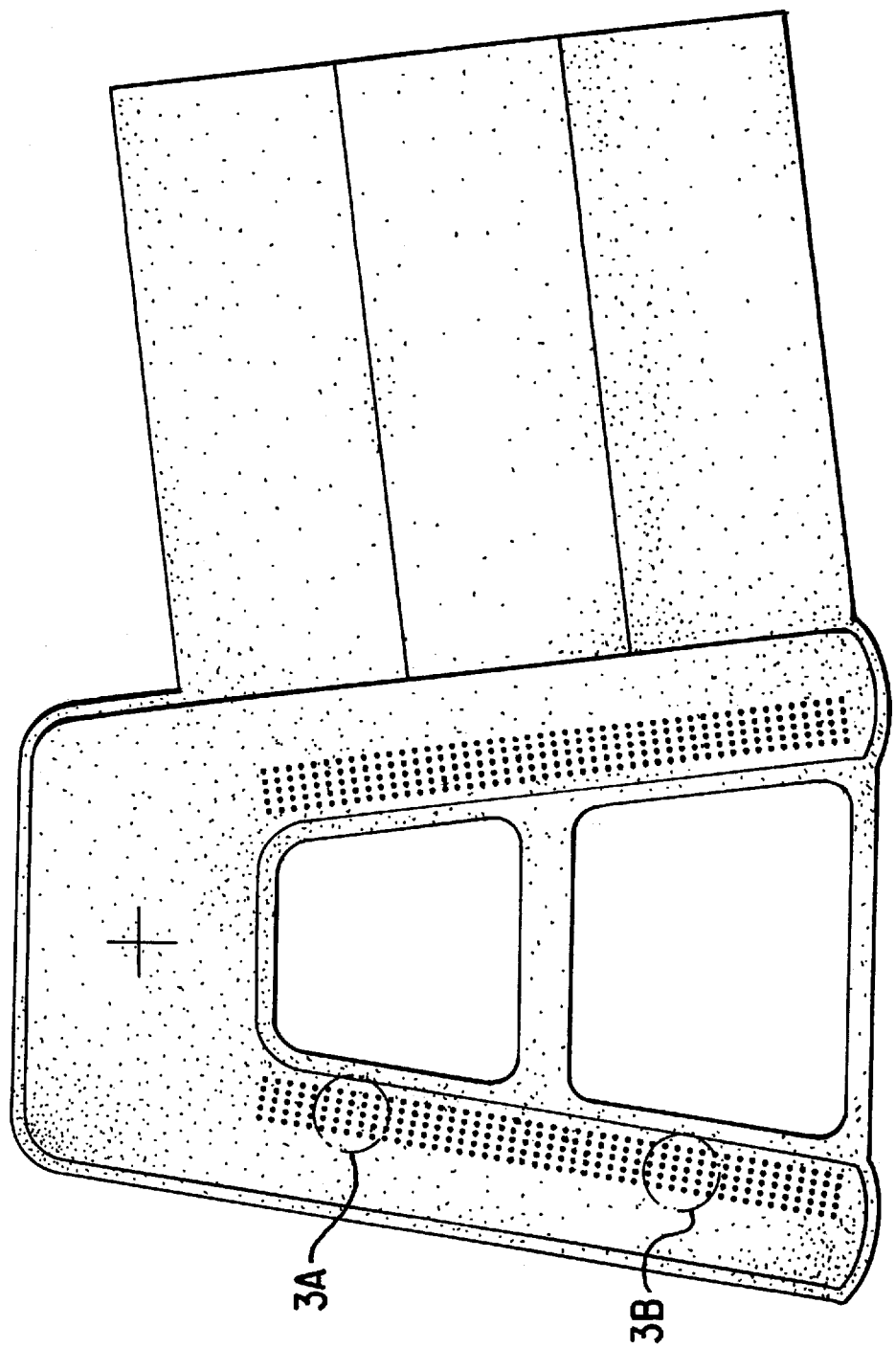
FIG. 2 is a top view of a preferred embodiment of a thermal conditioning apparatus for delivering a thermal medium to a patient according to the present invention.

Although the patient 1 shown in FIG. 2 is a child, the thermal conditioning apparatus for delivering a thermal medium to a patient according to the present invention is equally applicable to any patient, regardless of size or age. Note that the thermal conditioning of the medium used is dependent upon the desired result. If the patient suffers from hypothermia, or is undergoing a surgical procedure, it is desirable to bathe the patient with a warming medium. If the patient is suffering from hyperthermia, it is desirable to bathe the patient with a cooling medium. Furthermore, although in a preferred embodiment the thermal medium used is warm air, any thermal medium may be used in the thermal conditioning apparatus according to the present invention.

Unlike conventional patient thermal treatment systems which must be inflated and placed over the patient, or the patient placed within the thermal treatment system prior to inflation, the thermal conditioning apparatus according to the present invention is flexible in its operation. If desired, a patient may be advantageously placed within the thermal conditioning apparatus according to the present invention and the apparatus can be inflated only when needed without any movement of the patient or adjustment of the apparatus. On the other hand, a patient may be placed within an already inflated thermal conditioning apparatus according to the present invention. This option allows the patient to be thermally conditioned while any preparatory work is being performed. Thus, the thermal conditioning apparatus according to the present invention is flexible in its operation.

As noted above, the thermal conditioning apparatus 100 includes the first material layer 110, and FIG. 2 shows a top view of a thermal conditioning apparatus for delivering a thermal medium to a patient according to the present invention. In particular, the first material layer 110 includes numerous orifices therethrough, including a first plurality of orifices 200 and a second plurality of orifices 210. Note that the inlet portion 150 is located closer to the first plurality of orifices 200 than the second plurality of orifices 210. A thermal conditioning apparatus for delivering a thermal medium to a patient according to the present invention includes first and second pluralities of orifices, the first plurality of orifices being smaller than the second plurality. For example, the first plurality of orifices 200 are smaller than the second plurality of orifices 210. Thus, a lower volume of thermal medium is delivered to the patient through the first plurality of orifices 200, and a higher volume of thermal medium is delivered to the patient through the second plurality of orifices 210. Furthermore, the combined use of smaller orifices in close proximity to the inlet portion with larger orifices distal from the inlet portion tends to minimize the thermal gradients that may occur along the pair of extending portions.

In particular, as the thermal medium passes through the thermal conditioning apparatus, heat transfer occurs through the first and second material layers along the various flow paths of the medium. Thus, the thermal conditioning of the patient is more uniform than in conventional patient thermal treatment systems. Note that the transition point between the first plurality of orifices 200 and the second plurality of orifices 210 may occur at any point along the pair of extending portions. This transition point is dependent upon many thermodynamic factors such as, but not limited to, relative orifice size, incoming thermal medium's temperature, ambient temperature, volumetric flow rate of the thermal medium, the length of the extending portions, and the thermal characteristics of the material layers 110 and 120. In a preferred embodiment of the thermal conditioning apparatus for delivering a thermal medium to a patient according to the present invention, the transition point between first the plurality of orifices 200 and the second plurality of orifices 210 occurs substantially halfway along the length of the pair of extending portions. Note that any transition point may be utilized without departing from the scope of the present invention in its broader aspects. Also, it should be appreciated that other configurations of orifice sizing, spacing, and location could be considered within the broader aspects of the present invention.

The cover of a thermal conditioning apparatus for delivering a thermal medium to a patient according to the present invention includes a plurality of flap portions. For example, as shown in FIG. 2, the thermal conditioning apparatus 100 includes first, second, and third cover flap portions 220, 230, and 240 respectively. The use of multiple flap portions allows selective access to different regions of the patient's body during use of the thermal conditioning apparatus 100.

Figure 3A:
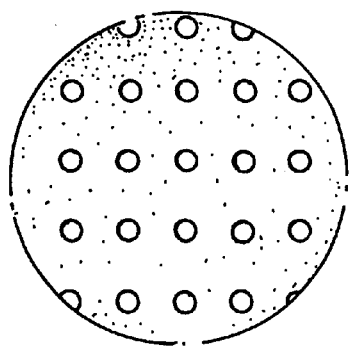
FIG. 3A is an enlarged partial sectional view of the area labeled 3A in FIG. 2 in accordance with the present invention.
Figure 3B:
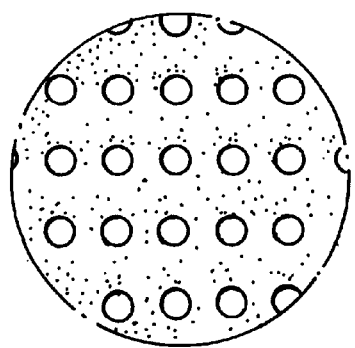
FIG. 3B is an enlarged partial sectional view of the area labeled 3A in FIG. 2 in accordance with the present invention.

FIG. 3A shows an enlarged partial sectional view of the area labeled 3A in FIG. 2, while FIG. 3B shows an enlarged partial sectional view of the area labeled 3A in FIG. 2. The relative size difference between the first plurality of orifices 200 and the second plurality of orifices 210 is readily apparent from FIGS. 3A and 3B. Of course, the relative sizes of the first plurality of orifices and the second plurality of orifices is dependent upon many thermodynamic factors such as, but not limited to, transition point between the first and second pluralities of orifices, incoming thermal medium's temperature, ambient temperature, volumetric flow rate of the thermal medium, the length of the extending portions, and the thermal characteristics of the material layers 110 and 120. In a preferred embodiment of the thermal conditioning apparatus for delivering a thermal medium to a patient according to the present invention, the first plurality of orifices 200 are 0.06 inches in diameter, while the second plurality of orifices 210 are 0.09 inches in diameter.

Figure 4A:
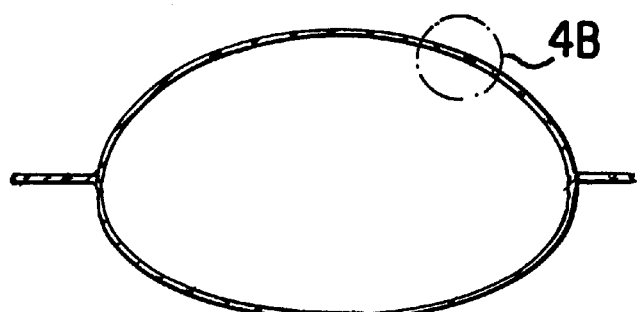
FIG. 4A is an enlarged sectional view taken along line 4A—4A in FIG. 1A in accordance with the present invention.

The manufacture of the thermal conditioning apparatus for delivering a thermal medium to a patient according to the present invention is best described with reference to FIG. 4A. The first and second material layers 110 and 120 are mirror images of each other. However, the first material layer 110 contains the plurality of orifices 130 therethrough. During manufacture, the first material layer 110 is laid on top of the second material layer 120. Heat is applied along the bonding portions 140 and the first and second material layers 110 and 120 are bonded together at these bonding portions. Thus, the inflatable medium delivery space 102 is formed between the first and second material layers 110 and 120. Likewise, heat is applied to the edges of under-patient strip portions 180 and 190 and the cover portion 170 to attach the first and second material layers 110 and 120 together. This heat bonding process of only two parts greatly reduces manufacturing time and cost.

In the preferred embodiment, at least one of the first and second material layers of the thermal conditioning apparatus for delivering a thermal medium to a patient according to the present invention includes an external surface layer and a coating layer. For example, FIG. 4B shows an enlarged partial sectional view of the area labeled 4B in FIG. 4A in accordance with the present invention.

Figure 4B:
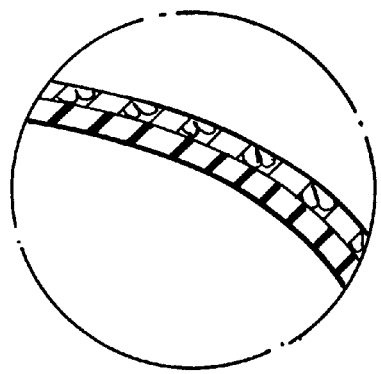
FIG. 4B is an enlarged partial sectional view of the area labeled 4B in FIG. 4A in accordance with the present invention.

FIG. 4B shows an enlarged partial sectional view of the first material layer 110 (with orifices omitted for clarity). As shown, the first material layer 110 includes an external surface layer 400 and a coating layer 410. The external surface layer 400 and the coating layer 410 may be constructed of any appropriate materials. For example, the external surface layer 400 may be constructed of any soft material suited for contact with a patient's body. Also, the coating layer 410 may be constructed of any non-permeable material to allow for inflation. Preferably, the external surface layer 400 is constructed of spunbond polypropylene. Also, preferably, the coating layer 410 is constructed of polyethylene. Thus, the polyethylene on the first material layer 110 bonds to the polyethylene on the second material layer 120 when heat is applied. Furthermore, the use of these material provides an improved thermal conditioning apparatus for treating a patient which may be folded for compact storage prior to its use.

Figure 5:
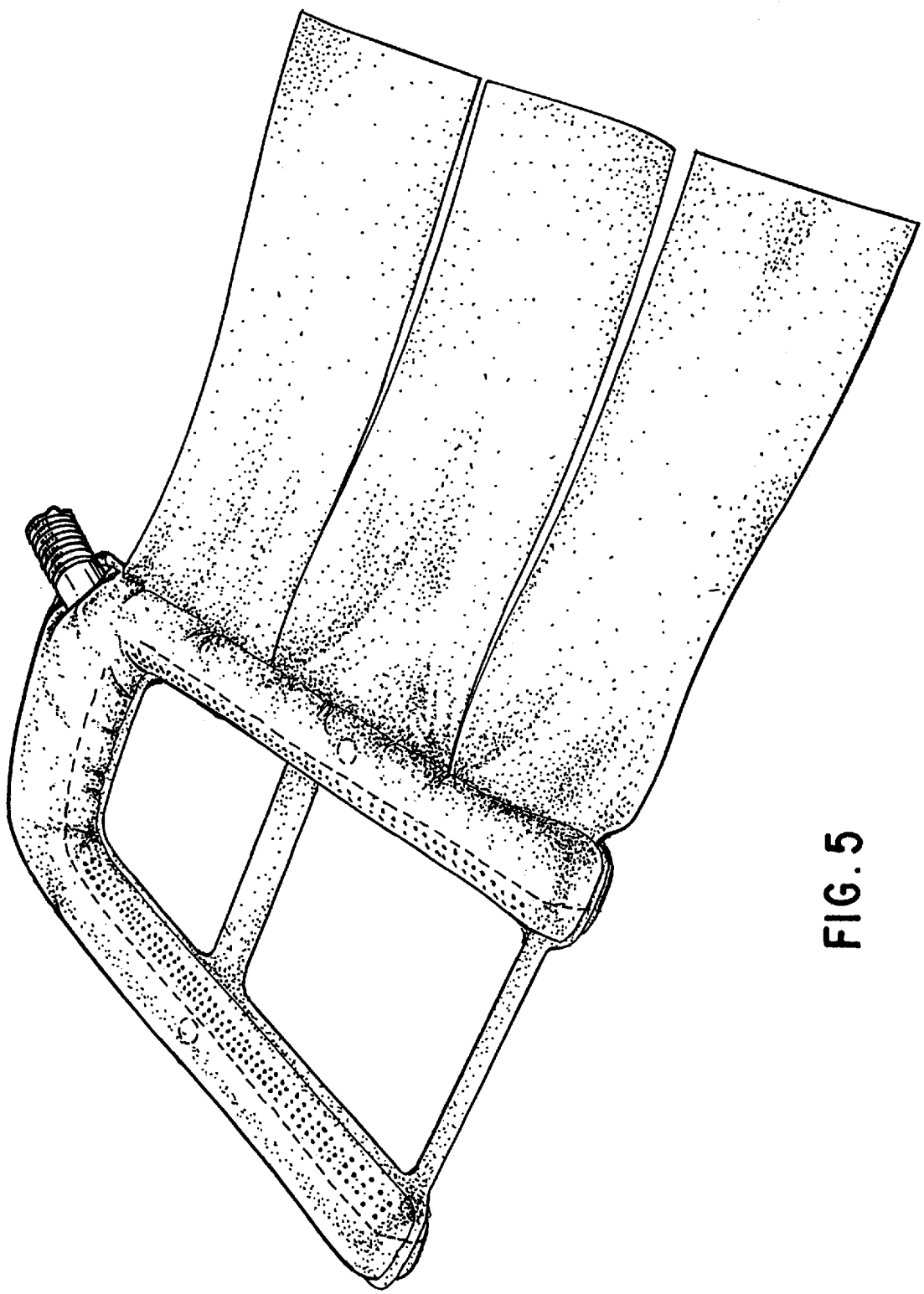
FIG. 5 is an isometric view of an alternate embodiment of a thermal conditioning apparatus for delivering a thermal medium to a patient according to the present invention in an inflated state.
Figure 1A:
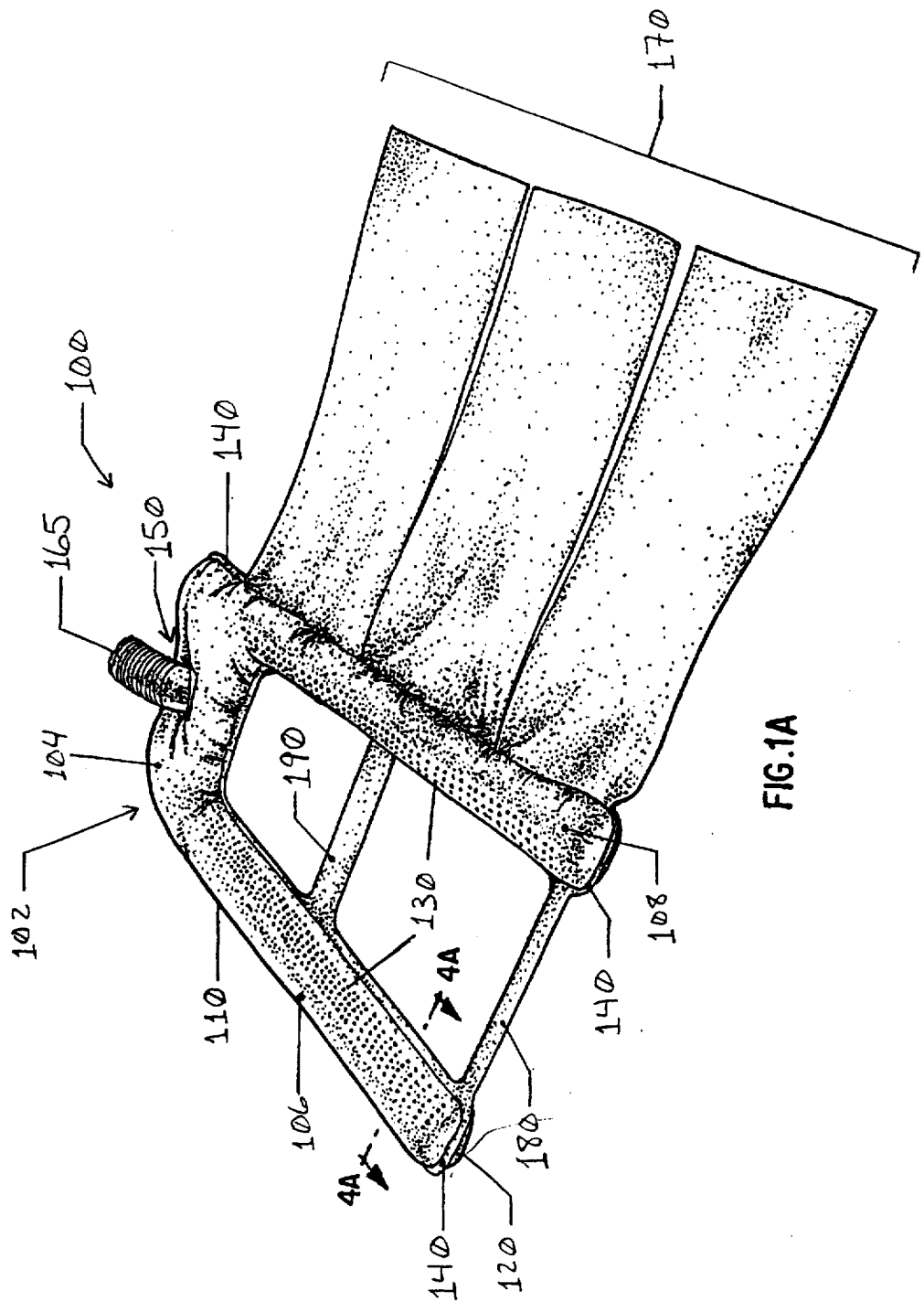
Figure 1B:
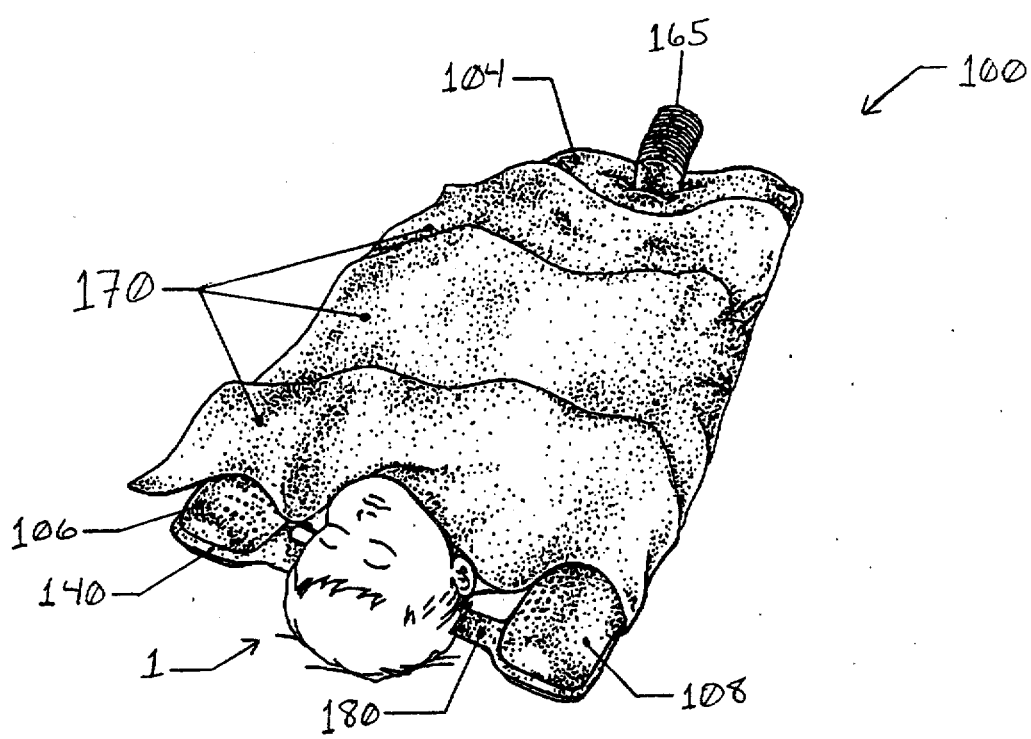
Figure 2:
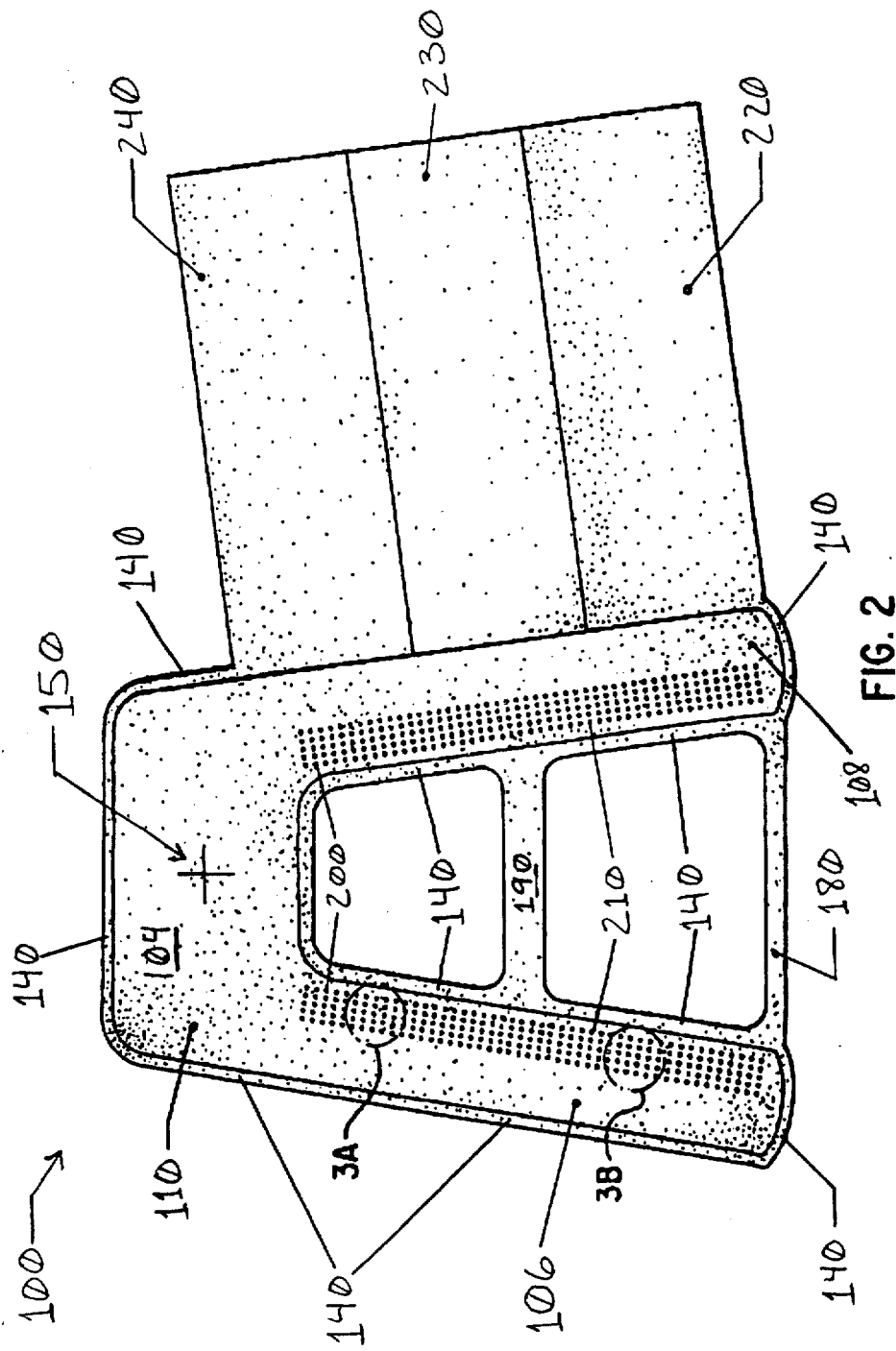
Figure 3A:
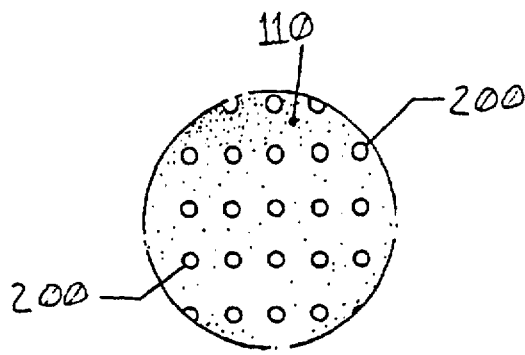
Figure 3B:
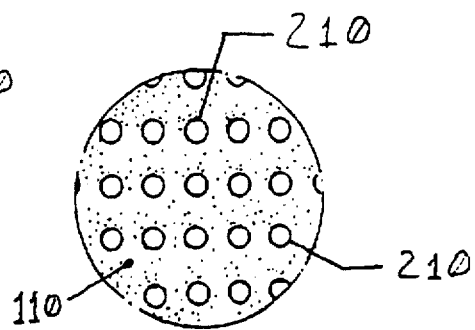
Figure 4A:
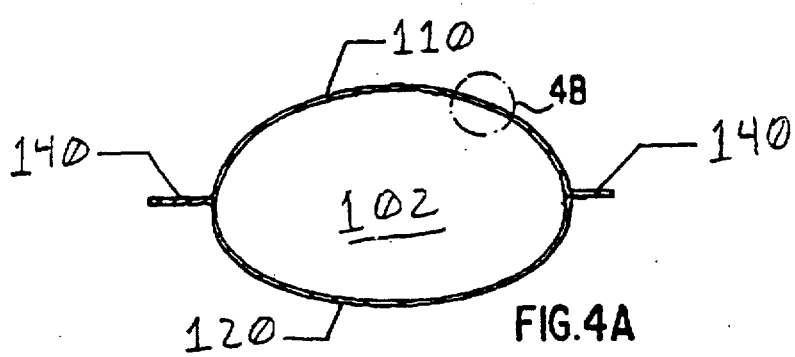
Figure 4B:
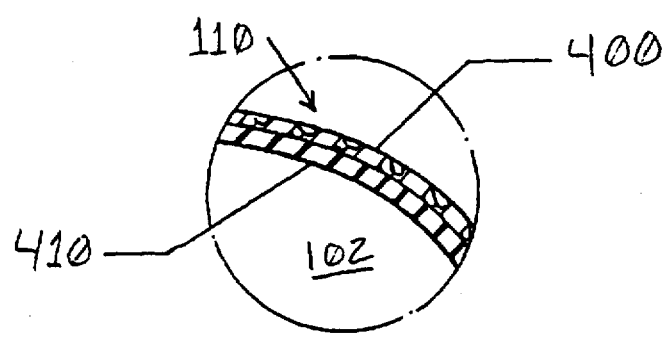
Figure 5:
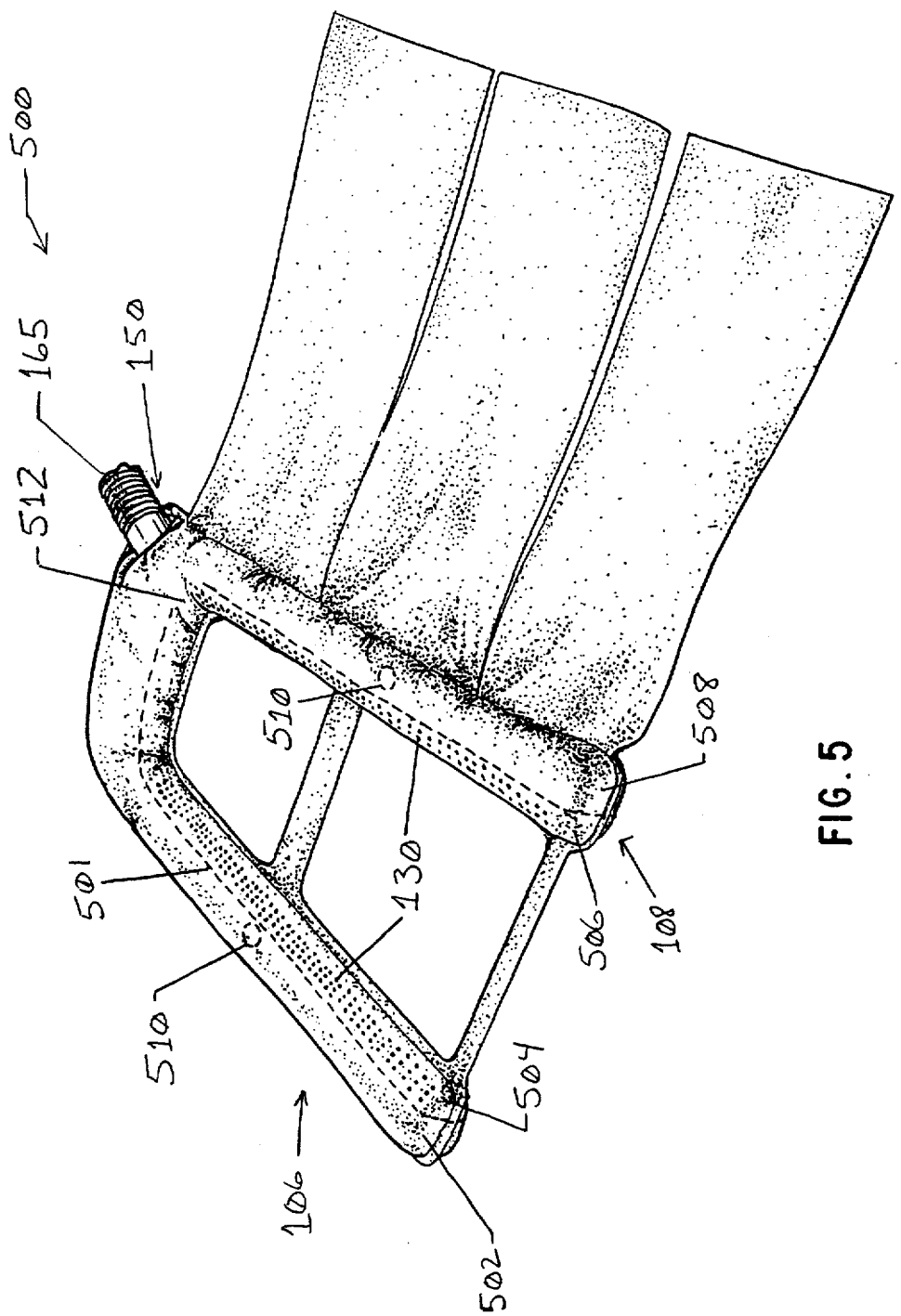

FIG. 5 shows an isometric view of an alternate embodiment of a thermal conditioning apparatus for delivering a thermal medium to a patient according to the present invention in an inflated state. In this alternate embodiment 500, the left and right extending portion 106 and 108 are each divided into two separate fluid delivery portions. The left extending portion 106 is made up of a left outer extending portion 502 and a left inner extending portion 504, while the right extending portion 108 is made up of a right outer extending portion 508 and a right inner extending portion 506. The outer and inner portions are separated by a partition 501. The orifices 130 are located only on the inner portions 504 and 506. Thus, the thermal medium is delivered to a patient via the inner portions 504 and 506 only. The thermal medium passing through the outer portions 502 and 508 is ejected through exit the orifices 510 located on the bottom of the thermal conditioning apparatus 500. Note that fluid communication between the inner and outer potions is achieved via an opening 512 in the partition 501. The use of the divided extending portions along with the exit orifices allows the thermal medium within the thermal conditioning apparatus 500 to be replenished more regularly, thus preventing stagnation of the thermal medium.

FIG. 5 also illustrates an alternate positioning of the inlet portion 150 along the header portion 104. In this embodiment, the thermal medium delivery hose 165 is located at an end of the header portion 104. This configuration allows free and open access to the patient along the majority of the header portion 104.

As illustrated in the detailed description, the thermal conditioning apparatus for treating a patient in accordance with the present invention substantially eliminates one or more of the problems or disadvantages found in the prior art. The novel structure, as particularly pointed out in the written description and claims hereof as well as the appended drawings, provides a thermal conditioning apparatus for treating a patient which is inexpensive, easy to manufacture, flexible in its operation, and provides a more uniform thermal treatment.

It will be apparent to those skilled in the art that various modifications and variations can be made in the thermal conditioning apparatus for treating a patient of the present invention without departing from the spirit or scope of the invention. Thus, it is intended that the present invention cover the modifications and variations of this invention provided they come within the scope of the appended claims and their equivalents.

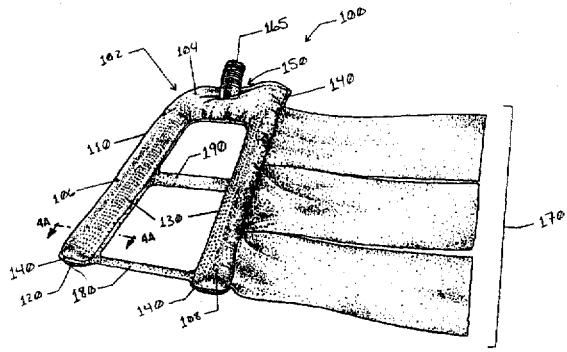

What is claimed is:

1. A thermal conditioning apparatus for delivering a thermal medium to a patient comprising:
    a first material layer having a substantially planar configuration;
    a second material layer having a substantially planar configuration, the first material layer bonded to the second material layer at portions thereof to define a pair of extending portions that are spaced to permit a patient to be positioned between the extending portions and to provide an inflatable medium delivery space therebetween;
    an inlet portion in connection with the medium delivery space to receive a thermally conditioned medium;
    a plurality of orifices on the pair of extending portions to deliver the thermally conditioned medium to the patient; and
    a segmented cover portion formed from the first and second material layers to extend laterally outward from one of the extending portions and of a length to permit folding the segmented cover portion over the patient and the respective pair of extending portions whereby selective portions of the patient may be exposed by opening a segment of the segmented cover portion.

2. The conditioning apparatus of claim 1, further including a non-inflatable under-patient strip portion extending between the pair of extending portions.

3. The conditioning apparatus of claim 2, wherein the plurality of orifices are open apertures and include different area sizes.

4. The conditioning apparatus of claim 2, wherein the non-inflatable under-patient strip is formed of the first and second material layers.

5. The conditioning apparatus of claim 1, wherein the pair of extending portions are internally bifurcated into an inner and outer chamber and only the inner chambers have the plurality of orifices.

6. The conditioning apparatus of claim 1, wherein the first and second material layers are further bonded to form a header portion and the pair of extending portions are disposed at ends of the header portion.

7. The conditioning apparatus of claim 6, wherein each of the extending portions extend linearly from a different end of the header portion.

8. The conditioning apparatus of claim 1, wherein the segmented cover portion comprises a plurality of flap portions.

9. The conditioning apparatus of claim 1, wherein the plurality of orifices comprise a first and second plurality of orifices, the first plurality of orifices being smaller in area size than the second plurality.

10. The conditioning apparatus of claim 9, wherein the first plurality of orifices are positioned closer to the inlet portion than to the second plurality of orifices wherein a lower volume of thermal medium is delivered to the patient through the first plurality and a higher volume of thermal medium is delivered to the patient through the second plurality.

11. The conditioning apparatus of claim 10, whereby the first and second pluralities of orifices are sized such that a thermal gradient along the pair of extending portions is minimized.

12. The conditioning apparatus of claim 1, wherein the thermally conditioned medium is warmed air.

13. The conditioning apparatus of claim 1, wherein at least one of the first and second material layers comprises an external surface layer and a coating layer.

14. The conditioning apparatus of claim 13, wherein the external surface layer comprises a spunbond material.

15. The conditioning apparatus of claim 14, wherein the external surface layer comprises spunbond polypropylene.

16. The conditioning apparatus of claim 15, wherein the coating layer comprises polyethylene.

17. A thermal conditioning apparatus for delivering a thermal medium to a patient comprising:
    a first material layer having a substantially planar configuration and including a first and second plurality of orifices, the first plurality of orifices being smaller than the second plurality;
    a second material layer having a substantially planar configuration, the first material layer bonded to the second material layer at portions thereof to define a substantially u-shaped inflatable medium delivery space of a configuration to extend about the sides of a patient;

an inlet portion in connection with the medium delivery space to receive a thermally conditioned medium and disposed closer to the first plurality of orifices than to the second plurality of orifices wherein a lower volume of thermal medium is delivered to the patient through the first plurality and a higher volume of thermal medium is delivered to the patient through the second plurality; and a non-inflatable cover portion formed of the first and second material layers and extending laterally from one of an extending portion of the u-shaped space and of a length to fold over and cover the patient, wherein the cover portion comprises a plurality of flap portions.

18. The conditioning apparatus of claim 17, further comprising at least one under-patient strip portion disposed between the pair of extending portions.

19. The conditioning apparatus of claim 18, wherein at least one under-patient strip portion is non-inflatable.

20. The conditioning apparatus of claim 19, wherein at least one under-patient strip portion is formed from the first and second material layers.

21. The conditioning apparatus of claim 17, wherein the first and second sets of orifices are sized such that a thermal gradient along the pair of extending portions is minimized.

22. The conditioning apparatus of claim 17, wherein the thermally conditioned medium is warmed air.

23. The conditioning apparatus of claim 17, wherein at least one of the first and second material layers comprises an external surface layer and a coating layer.

24. The conditioning apparatus of claim 23, wherein the external surface layer comprises a spunbond material.

25. The conditioning apparatus of claim 24, wherein the external surface layer comprises spunbond polypropylene.

26. The conditioning apparatus of claim 25, wherein the coating layer comprises polyethylene.

27. A thermal conditioning apparatus for delivering a thermal medium to a patient comprising:

a first material layer having a substantially planar configuration and including a first and second plurality of orifices, the first plurality of orifices being smaller than the second plurality;

a second material layer having a substantially planar configuration, the first material layer bonded to the second material layer at portions thereof to define a substantially u-shaped inflatable medium delivery space having a pair of extending portions of a configuration to extend about the sides of a patient;

a non-inflatable strip portion extending between the pair of extending portions for extending beneath the patient to hold the u-shaped inflatable medium space relative to the patient;

an inlet portion in connection with the medium delivery space to receive a thermally conditioned medium and disposed closer to the first plurality of orifices than to the second plurality of orifices wherein a lower volume of thermal medium is delivered to the patient through the first plurality and a higher volume of thermal medium is delivered to the patient through the second plurality; and a non-inflatable cover portion integrally formed of the first and second material layers and extending laterally from one of the extending portions of the u-shaped medium space and of a length to fold over the extending portion and cover the patient, wherein the cover portion comprises a plurality of flap portions whereby one or more of the flap portions can be selectively opened to expose a portion of the patient.

* * * * *

UNITED STATES PATENT AND TRADEMARK OFFICE
CERTIFICATE OF CORRECTION

PATENT NO. : 6,277,144 B1  Page 1 of 7
DATED : August 21, 2001
INVENTOR(S) : Kerry Tomic-Edgar et al.

It is certified that error appears in the above-identified patent and that said Letters Patent is hereby corrected as shown below:

Title page,
The title page showing the illustrative figure should be deleted and substitute therefore the attached title page.

Drawings,
Sheets 1-5, consisting of Figs. 1A, 1B, 2, 3A, 3B, 4A, 4B and 5, should be deleted and substitute therefore the corrected Figs. 1A, 1B, 2, 3A, 3B, 4A, 4B and 5, as shown on the attached pages.

Signed and Sealed this

Twenty-eighth Day of May, 2002

Attest:

JAMES E. ROGAN
Attesting Officer  *Director of the United States Patent and Trademark Office*

(12) United States Patent
Tomic-Edgar et al.

(10) Patent No.: US 6,277,144 B1
(45) Date of Patent: *Aug. 21, 2001

(54) THERMAL CONDITIONING APPARATUS

(75) Inventors: Kerry Tomic-Edgar, Santa Ana; Gordon Shigezawa, Irvine; Anthony V. Beran, Santa Ana, all of CA (US)

(73) Assignee: Respiratory Support Products, Inc., Irvine, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/167,663

(22) Filed: Oct. 7, 1998

(51) Int. Cl.⁷ ........................................... A61F 7/00

(52) U.S. Cl. ................................... 607/108; 607/112
(58) Field of Search .......................... 607/96, 108, 109, 607/110, 111, 112; 165/46; 5/421, 423

(56) References Cited

U.S. PATENT DOCUMENTS

| | | | |
|---|---|---|---|
| D. 359,810 | 6/1995 | Namenye | D24/206 |
| D. 362,507 | 9/1995 | Zuck et al. | D24/206 |
| 1,004,192 | 9/1911 | Phelan . | |
| 1,777,982 | 10/1930 | Popp . | |
| 1,965,424 | 7/1934 | Mascolo . | |
| 2,512,559 | 6/1950 | Williams | 5/347 |
| 2,579,964 | 12/1951 | Reynolds | 219/19 |
| 2,601,189 | 6/1952 | Wales, Jr. | 4/160 |
| 2,706,988 | 4/1955 | Weber . | |
| 2,930,594 | 3/1960 | MacCracken | 257/306 |
| 2,991,627 | 7/1961 | Suits | 62/3 |
| 2,998,817 | 9/1961 | Armstrong . | |
| 3,418,726 | 12/1968 | Sparks | 34/99 |
| 3,444,922 | 5/1969 | Dingman | 165/26 |
| 3,610,323 | 10/1971 | Troyer | 165/46 |
| 3,691,646 | 9/1972 | Ruffolo | 34/90 |
| 3,714,947 | 2/1973 | Hardy . | |
| 3,757,366 | 9/1973 | Sacher | 5/347 |
| 3,778,851 | 12/1973 | Howorth | 5/347 |
| 3,854,156 | 12/1974 | Williams | 5/347 |
| 3,867,939 | 2/1975 | Moore et al. | 128/254 |
| 3,881,477 | 5/1975 | Von Otto . | |
| 3,908,655 | 9/1975 | Lund . | |
| 3,942,202 | 3/1976 | Chevrolet | 5/348 |
| 4,121,571 | 10/1978 | Pickering . | |

(List continued on next page.)

FOREIGN PATENT DOCUMENTS

| | | |
|---|---|---|
| 113420 | 7/1984 | (EP) . |
| 0 311 336 A1 | 4/1989 | (EP) . |
| WO 97/14381 | 4/1997 | (WO) . |

Primary Examiner—Linda C. M. Dvorak
Assistant Examiner—R. Kearney
(74) Attorney, Agent, or Firm—Price and Gess

(57) ABSTRACT

The present invention relates to an improved thermal conditioning apparatus for thermally treating a patient. More specifically, the present invention relates to an inflatable apparatus for bathing a patient with a thermally conditioned medium. Such a treatment apparatus is useful for medically treating a patient suffering from hypothermia or hyperthermia, or for maintaining the body temperature of a patient undergoing a surgical procedure. A thermal conditioning apparatus according to the present invention includes first and second pluralities of orifices, the first plurality of orifices being smaller than the second plurality. An inlet portion which receives the thermal conditioning medium is located closer to the first plurality of orifices than the second plurality of orifices. The combined use of smaller orifices in close proximity to the inlet portion with larger orifices distal from the inlet portion tends to minimize the thermal gradients that may occur. Furthermore, a thermal conditioning apparatus according to the present invention includes a cover portion formed from the first and second material layers which make up the thermal conditioning apparatus.

27 Claims, 5 Drawing Sheets